US012239342B2

(12) United States Patent
Brader (10) Patent No.: US 12,239,342 B2
(45) Date of Patent: Mar. 4, 2025

(54) TRANSMYOCARDIAL JET PERFUSION DEVICE

(71) Applicant: Eric William Brader, Sewickley, PA (US)

(72) Inventor: Eric William Brader, Sewickley, PA (US)

( * ) Notice: Subject to any disclaimer, the term of this patent is extended or adjusted under 35 U.S.C. 154(b) by 0 days.

(21) Appl. No.: 17/551,609

(22) Filed: Dec. 15, 2021

(65) Prior Publication Data

US 2022/0183717 A1     Jun. 16, 2022

Related U.S. Application Data

(60) Provisional application No. 63/132,165, filed on Dec. 30, 2020, provisional application No. 63/132,192, filed on Dec. 30, 2020, provisional application No. 63/126,119, filed on Dec. 16, 2020, provisional application No. 63/126,130, filed on Dec. 16, 2020.

(51) Int. Cl.
*A61B 17/34* (2006.01)
*A61F 7/12* (2006.01)
*A61M 5/145* (2006.01)

(52) U.S. Cl.
CPC ...... *A61B 17/3421* (2013.01); *A61B 17/3403* (2013.01); *A61B 17/3478* (2013.01); *A61B 17/3496* (2013.01); *A61F 7/12* (2013.01); *A61M 5/145* (2013.01); *A61B 2017/3413* (2013.01); *A61B 2017/3419* (2013.01); *A61B 2017/3445* (2013.01)

(58) Field of Classification Search
CPC ............ A61B 17/3421; A61B 17/3403; A61B 17/3478; A61B 17/3496; A61B 2017/3413; A61B 2017/3419; A61B 2017/3445; A61B 17/3417; A61B 2017/00247; A61F 7/12; A61F 2007/0059; A61F 2007/0063; A61F 2007/0288; A61F 2007/126; A61M 5/145; A61M 2202/0472; A61M 2210/125; A61M 25/0631; A61M 25/0113
See application file for complete search history.

(56) References Cited

U.S. PATENT DOCUMENTS 2,438,643 A   3/1948   Moore
3,175,558 A   3/1965   Caillonette
(Continued)

FOREIGN PATENT DOCUMENTS

EP          0904797 A2    3/1999

*Primary Examiner* — Theodore J Stigell
(74) *Attorney, Agent, or Firm* — Barbara E. Johnson, Esq.

(57) ABSTRACT

The invention pertains to hardware and methods for direct injection, into the left ventricle of the heart of a patient or animal in cardiac arrest or in incipient cardiac arrest—using a 14-18 gauge cannula typically equipped with a retractable trocar—of an adequate amount of chilled saline or cryoprotective solution to create flow of chilled blood through the two carotid arteries, the two vertebral arteries, and the brain, to cool the brain or other vital organs. Generally, enough saline or cryoprotective solution is injected under high enough pressure to create a 30% baseline common carotid blood flow. The cannula arrangement with coordinated sharpened-tip retractable trocar, together with its surrounding flexible and rigid shield(s), diaphragm and stopcock(s), provides a sterile, self-sealing system suitable for use either in "the field" or in a hospital setting.

13 Claims, 6 Drawing Sheets

(56) References Cited

U.S. PATENT DOCUMENTS

| | | | |
|---|---|---|---|
| 4,326,520 A * | 4/1982 | Alley | A61M 25/0113 |
| | | | 604/159 |
| 4,552,149 A | 11/1985 | Tatsukee | |
| 4,750,493 A | 6/1988 | Brader | |
| 4,920,963 A | 5/1990 | Brader | |
| 6,120,520 A * | 9/2000 | Saadat | A61M 37/0069 |
| | | | 606/46 |
| 6,425,854 B1 | 7/2002 | Galt et al. | |
| 6,592,612 B1 | 7/2003 | Samson et al. | |
| 6,595,958 B1 * | 7/2003 | Mickley | A61M 25/0136 |
| | | | 604/164.01 |
| 2006/0058775 A1 | 3/2006 | Stevens et al. | |
| 2008/0319387 A1 | 12/2008 | Amisar et al. | |

* cited by examiner

TRANSMYOCARDIAL JET PERFUSION DEVICE

CROSS-REFERENCE TO RELATED APPLICATION

This patent application claims priority to, and incorporates herein by reference, each of the following four U.S. Provisional patent applications: U.S. 63/126,119 filed 16 Dec. 2020; U.S. 63/126,130 filed 16 Dec. 2020; U.S. 63/132,165 filed 30 Dec. 2020; and U.S. 63/132,192 filed 30 Dec. 2020.

BACKGROUND OF THE INVENTION

Field of the Invention

The present invention is a method of and apparatus for inhibiting tissue metabolism in the area of the brain and, more particularly, is a method and apparatus for inducing either localized therapeutic hypothermia or general therapeutic hypothermia, or both.

Description of the Background

Systemic hypothermia can dramatically postpone neurologic deterioration in hypoxic or anoxic tissues, and hypothermia has long been known to prevent brain damage during cardiac arrest. Though initially thought to be due to reduced metabolism, since oxygen reserves are depleted early on in hypothermic cardiac arrest, hypothermic inhibition of triggering events during ischemia and reperfusion injury are now thought to be responsible for hypoxic injury. So, hypothermia is now known to reduce tissue oxygen demand as well as to inhibit pathological processes which occur both during cardiac arrest and after return of circulation. For instance, accidental submersion in cold waters, and the commensurate systemic hypothermia thus produced, has consistently contributed to the neurologic survival of accident victims who otherwise would have sustained irreparable brain damage. Observation of this phenomenon led medical practitioners to induce systemic hypothermia in the course of various hypoxia and anoxia-producing surgical procedures in order to reduce both the systemic metabolism and the associated overall oxygen requirement of the patient as well as to inhibit deleterious processes.

In particular, hypothermia has been used extensively in cardiac and neurosurgical procedures where cardiac arrest must be induced to perform surgery safely. Hypothermia has also been used after return of spontaneous circulation after cardiac arrest to mitigate brain damage. While hypothermia induced before cardiac arrest is more effective than hypothermia induced after cardiac arrest, clinical trials have shown some benefit even to post-cardiac arrest hypothermia in some cases, and some EMS systems do employ prior art post arrest hypothermia at this writing. Hypothermia induced during cardiac arrest by external means has produced positive results in bench top studies and is performed in some centers already today, as an additional treatment alongside cardiopulmonary resuscitation (CPR). It should be noted that, while CPR is of benefit during cardiac arrest, it produces only approximately 10% of normal blood flow Which is not enough to prevent brain damage for any period of sustained CPR, which might be twenty minutes or longer. Under normothermic conditions, it is thought that approximately 30% of normal blood flow is needed to prevent brain damage. While external cooling may be of benefit during cardiac arrest and CPR, there is general consensus that only superficial brain structures would likely benefit from external cooling while deep structures would remain normothermic. In cases where cardiac arrest victims have suffered hypothermia, typically in a cold water drowning scenario, extended periods of cardiac arrest with CPR's being performed for several hours have nonetheless resulted in good neurologic outcomes. As a result, rapid induction of cooling, particularly of the brain, has documented promise in extending the current 20-minute barrier for CPR at normothermic conditions.

One of the current ways to improve results, vis a vis CPR, is the use of venoarterial extracorporeal circulation, or VA ECMO, in the treatment of cardiac arrest. Recent studies with early use of VA ECMO have improved cardiac arrest outcome markedly and with improvement in neurological outcome. In such patients, CPR is replaced with blood flow from the VA ECMO device, which mimics normal cardiac output and tissue perfusion. Once placed on a VA ECMO, the patient can be taken to a cardiac catheterization laboratory to open coronary blockages (possibly with stent insertion) so that the heart can then "be on its own again." Placing a patient on a VA ECMO is a highly technical procedure, and even in the best hands the operation requires ten minutes to perform, which severely limits downtime and transportation time to a center which can perform this therapy. The time required to institute VA ECMO operation also limits, to a lesser extent, utility of VA ECMO in a hospital setting, because delays of only a few minutes can profoundly negatively influence neurological outcome. VA ECMO, therefore, is an important technology for treating cardiac arrest patients, but there is nothing about VA ECMO per se that provides any sort of similar "buying time" benefit that hypothermia would achieve, were hypothermia to be induced in a similar context.

Currently, systemic hypothermia may be induced with less difficulty in the hospital environment, but at the present time emergency inducement of systemic hypothermia in a non-hospital setting is difficult or virtually impossible. As a result, induced systemic hypothermia currently forms no part of, for example, pre-hospital emergency cardiac arrest care such as cardiopulmonary resuscitation (CPR), notwithstanding the beneficial metabolic inhibition which such hypothermia would provide—and which is already widely known and well-established. Similar emergency procedures in which hypothermia has not been induced to date include the pre-hospital emergency care administered to patients in severe shock or stroke. As mentioned above, cooling after cardiac arrest is sometimes performed by paramedics via haphazard application of cold packs and informal infusion of cold intravenous fluids, but these cannot provide provide adequate systemic cooling in any sort of controlled way.

Apart from the above, induced localized hypothermia has been used widely in the non- or pre-hospital treatment of various physiologic conditions. Cold packs of some sort are standard equipment in first aid kits, and are used to decrease peripheral blood flow and commensurate swelling in the event of contusion, insect bites or stings, nosebleeds, sprains, etc. Cold compresses to the head, of course, have long been a standard symptom-relieving measure for headaches and fever. In addition to these common treatments, however, three of the less well-known uses for topical cold applications are described in U.S. Pat. Nos. 2,438,643, 3,175,558 and 4,552,149.

U.S. Pat. No. 2,438,643 discloses a pack, for use in local refrigeration anesthesia, which contains a plurality of waterproof compartments which contain brine and an absorbent material, such as sawdust. The pack may be cooled in any suitable refrigerating device and then used as a topical cold pack. Because the pack must be refrigerated, its utility for inducing localized hypothermia is limited to those areas for which refrigeration is available.

U.S. Pat. No. 4,552,149 also discloses a coolant-containing, refrigerant-dependent cold pack which is, more specifically, a head coolant device. The device comprises a main body consisting of a cooling piece for covering the top of the head and a plurality of cooling pieces radially arranged around the main body, for covering the front, sides, and back of the head. This head cooling cap is designed to inhibit hair loss during the administration of a drug or chemotherapeutic agent for Which hair loss is a known side effect. As with all cold packs which require refrigeration, the head coolant device is best suited to hospital and home application, and is not well suited for use in the types of pre-hospital emergency care for which traditional (powered) refrigeration is not commonly available.

U.S. Pat. No. 3,175,558 discloses a thermal therapeutic pack, specifically designed for postpartum application to the female perineum, which contains the unreacted constituents of endothermic reaction. The unreacted constituents are separated by frangible barriers, time-release capsules, or both, and the separation is maintained until the cold pack is needed. At the time of use, the reactants are admixed by, for example, manually cracking the frangible barrier between them, thus commencing the endothermic reaction and reducing the overall temperature of the cold pack and its contents. The pack is positioned on the patient, as desired, to cool the area of application by the reverse conductive heating of the pack by the body.

In several prior art devices, the cooling of the fluid in the device is accomplished through an endothermic reaction between water and ammonium nitrate, which are usually present as a single population of pellets. The amount and form of the reactants are generally chosen to produce a fluid that does not drop below freezing, to prevent tissue's becoming frozen and subsequently damaged. While avoiding tissue compromise, such conditions result in sub-optimal cooling of the patient.

As noted above, prior art patents and technologies for local cooling only possess deficiencies that preclude their effective use in the emergency treatment of cardiac arrest of severe shock in the field. The inventions disclosed in U.S. Pat. Nos. 4,750,493 and 4,920,963 addressed and overcame some of these deficiencies at an earlier time, by providing profound head cooling that to an extent could drive systemic cooling more effectively than topical cold packs could achieve. Even so, the devices disclosed therein were relatively bulky with preferred dimensions of 2'×2'×2'. In combination with their typical substantial weight (25 pounds or so), the devices were limited as to the areas where they could be stored and deployed, not to mention intrinsic limitations on the ability of external cooling application to create deep internal hypothermia of optimal precision and accuracy.

Thus, there remains an unaddressed need in the medical community for portable devices with limited physical profiles that provide for inducing controlled hypothermia for cooling of the cranial and extracranial areas. In addition, there remains an unaddressed need for rapid and deep cooling of patients and particularly brain tissue, while at the same time avoiding tissue damage from freezing. While presumably such an emergency method and system would require trained use by someone with expertise in paramedic treatment, at a minimum, the system would optimally be simple, easy to deploy, and easy to monitor—even "in the field" and away from a hospital setting.

SUMMARY OF THE INVENTION

In order to meet this unaddressed need, the invention pertains to direct injection, into the left ventricle of the heart of a patient or animal in cardiac arrest or in incipient cardiac arrest—using a 14-18 gauge cannula typically equipped with a retractable trocar—of an adequate amount of chilled saline or cryprotective solution to create flow of chilled blood through the two carotid arteries, the two vertebral arteries, and the brain, to cool the brain. Because the injection of chilled saline or cryoprotective solution prevents restarting the heart, the invention also embraces the use, on the animal or patient, of a VA ECMO, as described above as a well established heart/lung bypass device that provides both respiratory and hemodynamic support and which can be used in the field as well as in any health care setting. Any respiratory and hemodynamic support equivalent to the VA ECMO may be substituted for the VA ECMO. Generally, enough saline or cryoprotective solution is injected under high enough pressure to create a 30% baseline common carotid blood flow (as opposed to CPR, which generally creates only 10% of the same blood flow), typically 1-2 liters and virtually never more than 2, liters for a patient of average height and weight. The cannula arrangement with coordinated sharpened-tip retractable trocar, for selective puncturing through the skin and thence directly into the left ventricle of the heart, together with its surrounding flexible and rigid shield(s) and stopcock(s), provides a sterile, self-sealing system suitable for use either in "the field" or in a hospital setting, in connection with a VA ECMO or even a simpler electric or even manual pump for continuous or pulsatile fluid injection.

DETAILED DESCRIPTION OF THE INVENTION

As described immediately above, the invention pertains to direct injection, into the left ventricle of the heart and using a 14-18 gauge catheter, or its equivalent, of an adequate amount of chilled saline or cryoprotectant fluid to create flow of chilled blood through both the carotid arteries and both the vertebral arteries and into the brain, to cool the brain. Longer and continuous injection of chilled saline or cryoprotectant fluid can create a more generalized hypothermia when needed, such as during the emergency treatment of cardiac arrest or severe shock. Systemic hypothermia, for a limited time, is often appropriate to ameliorate the negative consequences of stroke. Because the injection of chilled saline or cryoprotectant fluid prevents the heart's restarting due to the cold temperature, the invention also embraces the use of a VA ECMO (or its equivalent), a well-established (known in the art) portable heart/lung bypass device that provides both respiratory and hemodynamic support and can be used in the field as well as in health care settings. Any respiratory and hemodynamic support device or protocol equivalent to the VA ECMO may be substituted, in connection with the inventive concepts described herewith. Generally, enough saline or cryoprotectant fluid is injected under high enough pressure to create a 30% baseline common carotid blood flow—as opposed to CPR, which generally creates only 10-20% common carotid blood flow. As described in detail below, the cannula arrangement with coordinated sharpened-tip retractable trocar, for selective puncturing through the skin directly into the left ventricle of the heart, together with its surrounding shield(s) and stopcock(s), provides a sterile, self-sealing system suitable for use either in "the field" or in a hospital setting.

Figure 1A:
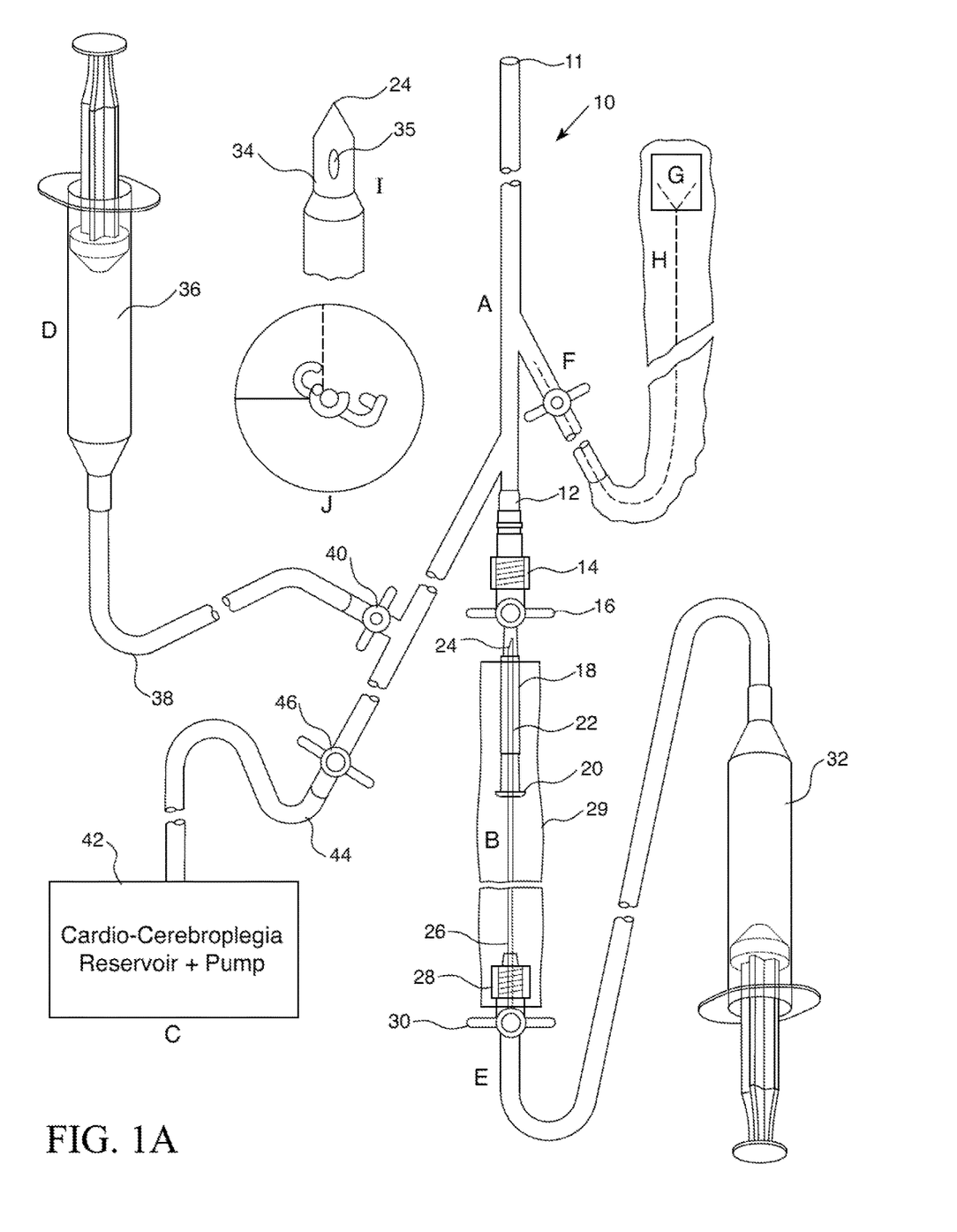
FIG. 1A is a schematic showing the features of the present system, including but not limited to trocar, stopcock(s), diaphragm, flexible sheath, and resilient sheath, all in a closed, sterile array.

Direct left ventricular puncture is the best injection site for cold saline, for reasons which include the following. Only one puncture is needed to perfuse the entire cerebrovascular system, when using the left ventricle. The left ventricle is thick and will usually self-seal from small diameter punctures such as a trocar/14-18 gauge cannula might create or leave. Even if leakage were to occur, having a functioning aortic valve while on VA ECMO would limit bleeding, with VA ECMO providing rapid transfusion and continued perfusion. Optionally, using the optional guide wire embodiment (see FIG. 1, modules F, G and H) would allow percutaneous closure if needed. In a cardiac arrest scenario, it is easy to find the left ventricle. By contrast, individual arteries are smaller, more difficult to locate and manipulate in a cardiac arrest situation, are more difficult to cannulate than the left ventricle, do not self-seal as easily as does the left ventricle and often have plaques that could be inadvertently struck and released, causing potentially disastrous embolization. For these reasons trying to cannulate blood vessels, rather than the left ventricle, is untenable for injecting cooling fluids. By using high pressure infusion into the left ventricle, additional flow can be entrained via the Venturi effect initiated by the high-pressure flow. Given the thick wall of the left ventricle, these high infusion pressures will be better tolerated than by any thin-walled blood vessel. Injection and infusion of cold fluid into the left ventrical, rather than into any other veins or arteries, is therefore preferred in the context of the present technology. The fluid itself may be cold saline, cold protective fluids, or any cold solution that is otherwise suitable for infusion into the circulatory system of an animal or patient in need of cooling.

Figure 2:
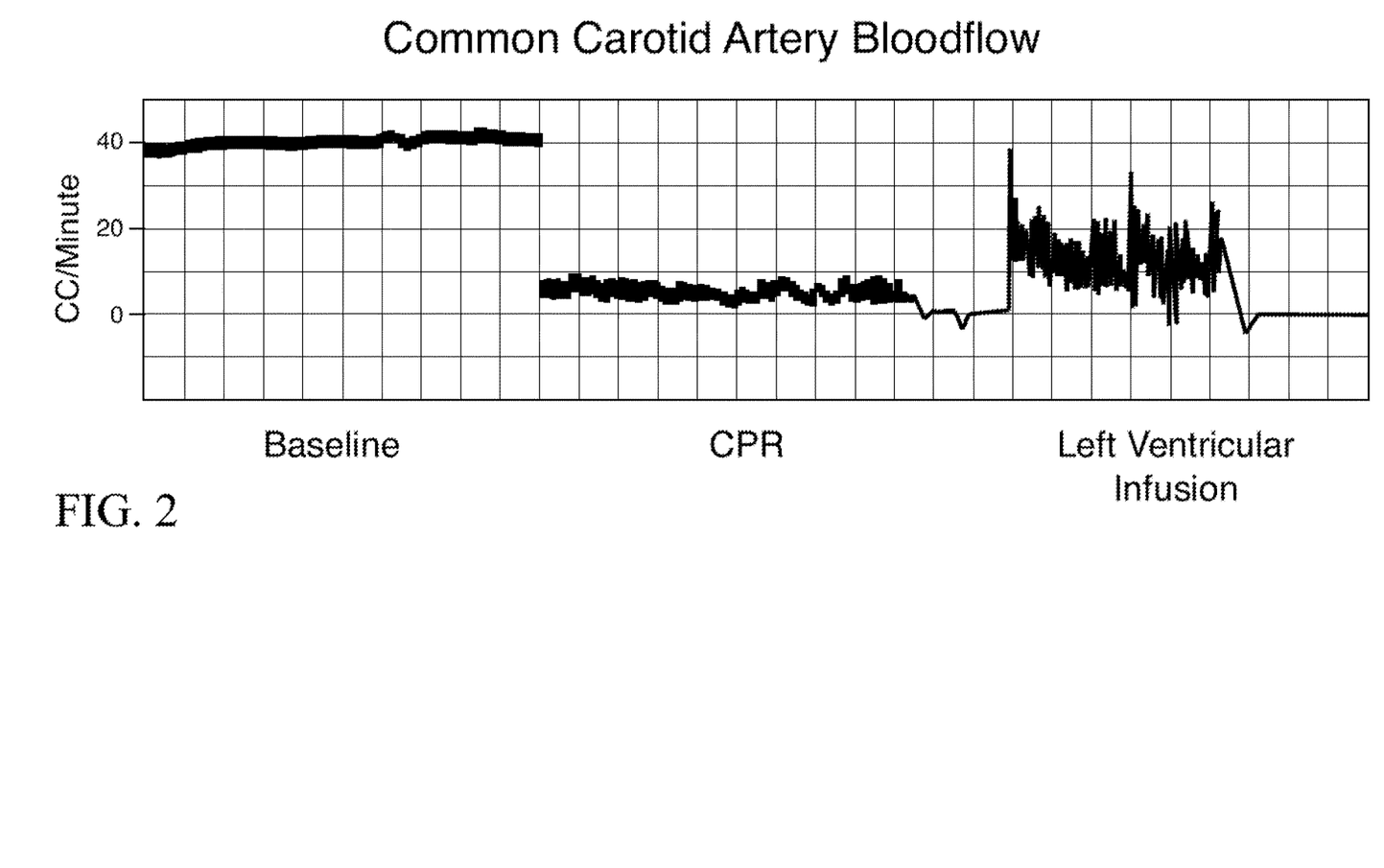
FIG. 2 is a line graph showing the results of a pilot study comparing and contrasting blood flow, in CC/minute, during left ventricular infusion versus cardiopulmonary resuscitation, as compared to baseline.

More particularly, therapeutic cerebral and systemic hypothermia can be rapidly and easily achieved with the following techniques and hardware. Percutaneous left ventricular cannulation by a small diameter cannula (14-18 gauge), typically fitted with a retractable trocar for initial cutting and perforation, with a high pressure infusion of cooled cardiocerebroplegia fluid into the left ventricle can rapidly induce a state of protective/therapeutic hypothermia in cardiac arrest. A pilot study indicates that this technique can achieve 30% of baseline cerebral blood flow for short time period (FIG. 2). As such, rapid brain cooling can be achieved very quickly. While some have speculated that a similar effect could be achieved by inserting cannulas within the carotid arteries, as described above this would be technically much more difficult to do than intra-ventricular infusion, with insertion needed in both carotid arteries, entailing placing cannulas into smaller targets and risking breaking off arteriosclerotic plaques, which would likely cause strokes in the patient. When fluids are introduced into the left ventricle, forward flow is generated by increasing pressure in the left ventricle, causing the mitral valve to close and the aortic valve to open. By using a high pressure jet, blood within the circulatory system is entrained, thereby increasing the effective volume of the perfusate. Left ventricular assist devices (LVAD) entail open surgical implantation of a cannula within the left ventricle on a semipermanent/permanent basis with extended replacement of cardiac output. By contrast, the present device is designed to be a temporizing (temporary) measure to achieve brain and organ protection, with likely reinstitution of CPR after the infusion is complete. Only a limited amount (no more than 2 liters in general) of fluid can be infused in this manner, since there is no recirculation of fluid back into the pump and volume overload within the patient would occur if permitted to continue for an indefinite period. Due to the reduction in brain and body temperature, CPR blood flows—although inadequate during normothermia—become adequate to preserve tissue and especially vulnerable brain matter. By using pulsatile flow (discussed further below) it is also thought that more filling in between jets within the left ventricle with the patient's own blood will occur, thereby increasing the volume of the perfusate and allow perfusion at a more effective level than typical CPR. The cold cardiocerebroplegia fluid is kept at a relatively lower temperature since a greater volume of the patient's own blood would need to be cooled with each jet.

As described more particularly below in association with the Figures, a rigid, likely metallic, trocar/cannula insertion device is needed to penetrate into the left ventricle, as opposed to more simple percutaneous intravascular devices, because a strong puncture arrangement is needed to traverse all the tissue layers that need to be penetrated, including the wall of the left ventricle, in order to access the left ventricular cavity. Using a stronger and more rigid cannula will prevent kinking and crimping during and after insertion. (A more flexible, less sturdy cannula would be more subject to migration after insertion and to "catheter whip" which could be deleterious to the left ventricle.) A rigid cannula will also allow better directability of the jet towards the left ventricular outflow tract/aortic valve. Small diameter cannulas are also known to be able to be removed from the left ventricle in a high percentage of cases without the need for surgical procedure to close the ventricle insertion tract. Since the patient will typically be placed on VA ECMO anyway, and perfusion from the VA ECMO device will be coming from the opposite direction up the aorta, the aortic valve will block any loss of blood from any persistent laid-open tract within left ventricle until spontaneous circulation is restored. Since it is thought that a state of cerebral and systemic preservation will be achieved, restarting the heart immediately in the field is not a concern, since the CPR limit without brain damage may be extended to several hours from clinical data in accidental hypothermia cases. In one emulation, FIG. 1A (see modules F-G-H) a guidewire may be inserted within the tract extending from the site of puncture into the left ventricle. By keeping the wire in place, commercially available plugging materials can be threaded over the wire and used to plug the left ventricular tract if need be. Additionally if one desires to reinsert the cannula, it could also be threaded over this wire. Wires uniquely constructed with the outer component constructed of a malleable pretreated sheath, and which will fold up/accordion, can prevent loss of the wire within the tract. A simple sterile dressing can be placed over the outer segment of the wire to maintain its sterility.

The present device also has multiple features to verify optimal positioning. If an ultrasound device is available, optimal position can be ascertained by this technique if the clinician is skilled in ultrasound use. To permit verification of cannula position, the trocar must be constructed in a way which allows for aspiration of blood from the left ventricle after the left ventricle has been punctured. This will confirm appropriate placement when cannula insertion is done "blindly," that is, without ultrasound or any other imaging guidance. Typical trocars are of solid construction, but the present trocar is either hollow or is fitted with a side channel that allows blood flow, discussed in greater detail below (although the trocar must be solid at its cutting tip). The need for solidity at the trocar cutting tip is—if a trocar were constructed like the stylette of an IV catheter (essentially being a hollow trocar) which is centrally hollow out through the tip, the cutting tip could produce coring of the punctured tissue. This coring would then likely result in embolization, after the present infusion began. A completely hollow trocar tip could also interfere with attempts to aspirate blood from the left ventricle to confirm positioning of the present cannula. Therefore, several embodiments of any cutting shape ("pencil point," hexagon, and so forth) for the present trocar are contemplated. These would all require a solid or predominantly solid sharp trocar tip of varying geometry however, the central portion of the trocar (not the tip itself) will be hollow starting at its "bird's eye" near the cutting tip. The bird's eye creates a conduit by which fluid (containing blood) flow may be "pulled back" to satisfy the practitioner that the trocar/bird's eye/cannula are indeed positioned correctly in the left ventricle. If one is using ultrasound, proven positioning can be further verified or optimized by visualizing flow created within the left ventricle. As explained further with respect to the Figures, the trocar can be retracted within a sealed system, rather than removing the trocar altogether after initial deployment, to allow reinsertion of the trocar to reconfirm cannula positioning with "aspiration," without introducing external contamination or incidental introduction of air, by drawing blood/fluid back through the bird's eye to establish left ventricular positioning. Additionally, instead of containing a hollow center, the trocar can beneficially be externally grooved in such a fashion that allows aspiration from the left ventricle, and the groove creates a de facto hollow passage when the trocar is in place in its snug fitting cannula. For practical reasons, mostly due to the narrow gauge of the trocar, it is generally easier and stronger to construct a grooved trocar than a hollow trocar. Such a grooved trocar may have application in other medical areas in which cannulas or catheters are placed and one wishes to sample fluid or even inject fluid prior to trocar removal. A grooved trocar can also be used when an obturator is used in an insertion procedure, that is, with obturators' essentially being rounded tipped trocars. In particular, insertion of a cerebral intraventricular catheter could be an application for the present grooved trocars, as removal and obturator replacement is necessary repeatedly to determine whether the tip of the cannula is within the ventricular spaces of the brain. As constructed and as discussed further below, the trocar can be withdrawn upon successful placement of the cannula within the left ventricle and housed within the sterile confines of the present device, with the needle's being sheathed to protect from inadvertent needle puncture of patient, operator or bystander. Should one wish to remove the trocar entirely from the device, this is also an option given the positioning of the stopcock through which the trocar is threaded. The clear sheathing material would be easily torn from the aforesaid stopcock, and the diaphragm through which the trocar tip is initially inserted may be and should be made of self-sealing polymer. There is an additional port (D) (see FIG. 1A) which will allow repeat aspiration for purposes of reverifying cannula position during the infusion process as needed.

The device is composed, optimally, of a completely sealed percutaneous transmyocardial cannula/trocar device for use in association with a cardio-cerebroplegia reservoir/pump (FIG. 1, items A-F, I and J) with an optional Seldinger type wire feature (FIG. 1, items F. G and H) to mark the tract of insertion in the left ventricle. All these features are disclosed further, and explained, in connection with the accompanying Figures.

Referring now to FIG. 1, Module A contains the main cannula 10 of the present invention. It is inserted with the use of a specially designed trocar illustrated in Module B and is designed to be used in concert with the main cannula 10. The main cannula 10 is in the 14 to 18 gauge or equivalent catheter size range. The main cannula connects to the cannula fitting 12 via a cannula fitting connector 14. The cannula fitting connector is typically a threaded male/female connector but may be any connector (snap in, press fit, etc.) that can similarly maintain a fluid-sealed, sterile system. Adjacent the cannula fitting connector 14 is the distal stopcock 16. The distal stopcock 16 is directly connected to a distal stopcock rigid housing 18, which is a hollow tube connected to the stopcock at the distal end of the tube whereas the proximal end of the hollow tube is completely covered by a rigid housing diaphragm 20 (it is the housing that is rigid, not the diaphragm 20 itself, which is flexible and usually self-sealingly permeable). The rigid housing diaphragm 20 is fashioned of a flexible resilient polymer which can be breached (punctured) by the present trocar but which is optimally self-sealing upon retraction of the trocar. As shown in FIG. 1A, the trocar 22 has already been pushed through the rigid housing diaphragm 20 and the trocar cutting tip 24 is shown in position just proximal of the distal stopcock 16, where the trocar cutting tip 24 is completely sheathed and cannot puncture any operator, patient or bystander.

An important thing to appreciate about FIG. 1A is that the linearly connected trocar base 26, trocar 22 and trocar cutting tip 24, all representing long, continuous structures, are much lengthier than is shown in FIG. 1A, hence the breakaway portion of the drawing at Module B. The trocar 22 needs to be long enough to extend, as it traverses within the main cannula 10, to exit the cannula distal tip 11 to serve as the cutting edge to traverse the patient's tissues starting at the skin of the chest and down into position in the left ventrical of the heart. After positioning of the trocar 22 and its coordinating main cannula 10, the trocar 22 can be retracted back into the position shown in FIG. 1A, where it is out of the way but still housed within a sterile, closed environment as further described below.

Sterility (pre-sterilization) of the pre-assembled construct of FIG. 1A, particularly the main cannula 10 and its associated structures shown in segments A and B, is largely made possibly by the flexible sheath 29. The flexible sheath 29 can be made of any flexible polymer material and will be generally much longer than is shown in FIG. 1A—perhaps from 4 to 12 inches or more, up to 20 to 24 or 30 inches approximately. The flexible sheath 29 allows the trocar 22 to pass through the main cannula 10 to exit the cannula distal tip 11—because there is enough slack in the flexible sheath to permit this—and yet the trocar can then be retracted without affecting the closed environment within the flexible sheath 29. As shown in FIG. 1A, the flexible sheath 29 extends from and encloses (in a sterile field created by means known in the art) the area between the distal end of the distal stopcock rigid housing and the proximal stopcock, but the flexible sheath actually needs only to extend from the proximal end of the distal stopcock rigid housing to the trocar connector 28, as long as the interior of the flexible sheath is sealed and maintained without breach (other than the breach introduced by the cutting end of the trocar 22 itself into the diaphragm 20). In this way, if the trocar 22 is inserted into the patient, later retracted, and then subsequently needs to be reinserted in the patient, the sterile field of the insertion site will have been maintained throughout, especially upon selective closing of the distal stopcock 16 as needed.

The trocar base 26 is solidly anchored in the trocar connector 28 in FIG. 1A, but everywhere else along the trocar 22 length the trocar 22 is free to pass forwards (distally) and backwards (proximally) through the main cannula 10—assuming the distal stopcock 16 is in the open position.

Fluid flow into the main cannula 10 ultimately is introduced through the fluid syringe 32 or its functional or structural equivalent—a manual pump, a hand pump, or other fluid injection device. While the main cannula 10 is being put in place, the proximal stopcock 30 is kept in a closed position. When cold fluid injection is to begin, the proximal stopcock should be manually opened and kept in an open position throughout fluid introduction into the system.

During placement of the main cannula 10, especially in the field and in the absence of any guidance from ultrasound to place the trocar cutting tip 24 and the main cannula 10 into the left ventricle of a patient to be treated, there needs to be a way to confirm that the cannula placement is correct. (Of course ultrasonographic or fluoroscopic guidance may be used to place the main cannula 10, but in the field such guidance may not be available.) One way to confirm correct placement of the cannula distal tip 11 is to open the aspiration stopcock 40 and "pull back" on the aspirating syringe 36, to be sure there is blood return from the cannula distal tip 11 in position in the left ventricle (and the associated left ventricle blood supply). This return can best be returned while the trocar is still in initial inserted position, drawing blood back through the bird's eye 35 into the trocar 22 and thence into the aspiration syringe 36 where the blood return can be viewed. Blood return can also, of course, be confirmed even after trocar retraction, through the cannula tip 11 and back into the aspiration syringe 36. The point of the aspiration syringe 36, then, is to provide a simple, mechanical confirmation that the cannula distal tip 11 is indeed in correct position in the cavity of the left ventricle of the heart. Of course the aspirating syringe 36 is fitted with its own aspirating cannula 38 interconnected to the aspiration stopcock 40. After initial placement of the trocar 22 into the patient, which concomitant positioning of the cannula distal tip 11 is within the left ventricle, the only stopcock in the system that is in an open position, initially, is the aspiration stopcock 40, to allow the user "to pull back" to confirm a blood return. When blood return is confirmed, the aspiration stopcock 40 is closed, and both of the distal stopcock 16 and the proximal stopcock 30 are opened to allow passage of cold fluid, from the fluid syringe 32, into the main cannula 10 and thence into the patient's left ventricle (as assisted in some cases by Module C reservoir and pump connected thereto).

An optional feature shown in FIG. 1A is the module F-G-H, which provides a Seldinger wire for placement assistance. Seldinger wires are known in the art, although never before used in a system according to the present invention. A Seldinger wire can be inserted down the cannula and into the left ventricle to maintain the insertion tract, should one wish to withdraw the entire main cannula 10 (not just the trocar 22) but also want to reinsert the cannula again later. The Seldinger wire has a flexible removable flange enabling advancement through the infusion cannula. Upon exiting the tip of the infusion cannula the plan would unfurl, preventing the wire from being lost within the patient, that is, the unfurled structure shown in Module G holds the wire in place within the patient, so the wire does not inadvertently get pulled out, or fall out. This Module G option would enable re-insertion of a another catheter of cannula besides the initial cannula, if necessary, or would facilitate introduction of a left ventricular wall closure device if desired or needed.

Referring again to the trocar 22, with the trocar 22 in the fully inserted position in the patient, the tip of the trocar—of which the trocar cutting tip 24 is pictured in the loaded (extended) position in the Module labeled I—is used to puncture the chest wall in an orientation optimized to enter the left ventricle successfully. As described above, the trocar is a special hollow of grooved trocar with at least one bird's eye hole so that the trocar is not hollow (or grooved) the whole way to its distal tip. After confirming the cannula/trocar is thought to be within the left ventricle, the proximal stopcock 30 is then opened and the trocar flushed with the ultrasound on Doppler mode (if available) to verify positioning and good flushing within the left ventricle. If using fluoroscopy, IV contrast dye is contained within the flush syringes, or saline with Doppler, but as discussed above the aspiration syringe 36 can be used to pull back blood for verification when fluoroscopy or Doppler guidance are not available, because it is possible (albeit not optimal) to insert into the left ventricle blindly, using only anatomic landmarks. The main cannula 10 is best composed of steel as well as the trocar 22, however, equivalent materials may be substituted. Given that multiple tough tissue layers will need to be penetrated by the trocar/cannula device, a plastic cannula could prove difficult to insert and could "accordion" whereas steel does not. Steel will also be more easily, seen on ultrasonographic or fluoroscopic viewing, although sufficiently strong plastic cannulas can be impregnated with ultrasonographic or radiologic marking materials as desired. After the cannula/trocar is deemed to be in appropriate position within the left ventricle, the cannula may be attached to the skin by a attachment device labeled as J which will also preserve puncture site sterility. If after initial jet perfusion it is anticipated that the cannula will be immediately or promptly removed, module J would not necessarily be needed. The trocar will then be withdrawn to a length limited by flexible sheath 29. If deemed necessary, the trocar 22 could be removed completely from the system by tearing the flexible sheath 29 and closing the pictured stopcock to prevent air leakage back into the system.

After one is ready to begin jet perfusion, the proximal stopcock 30 can be turned on and an additional flushing as a final verification of position can be performed. The proximal stopcock 30 will be turned to the closed position and the module C-cardio-cerebroplegia reservoir and pump turned to the open position (including stopcock 46)—and the cardio-cerebroplegia solution, presumably or usually (but not necessarily) cold, can be infused under high pressure with a powered pump, a mechanical pump, or even a manual pump. In other words, fluid pumping can be achieved by electric motor or by any manual mode of pumping if in a field use modality (FIG. 1A, Module C). The reservoir requires a capacity in the neighborhood of two liters. The flexible sheath 29 with the trocar 22 retracted will prevent air from entering the system via the Venturi effect, after jet perfusion begins, especially when the distal stopcock 16 is also closed.

As described in part above, Modules G and H, like Module F, are optional modifications and represent additional features to a standard guidewire, contained within a transparent airtight wrapper also. If one would wish to keep a guidewire in place but wish to remove the cannula, the guide wire would be advanced in the standard fashion with the attached flange G preventing loss of the proximal tip of the guide wire within the cannula device-module A. Once the cannula device-module A is removed, the wire can be manually secured distal to the now retracted cannula at the puncture site above the skin. In order to completely remove the cannula the flange G would be snapped off of the specially designed proximal module H of the guide wire. This will permit the passage of the guide wire through the cannula-module A so that the jet perfusion device can be completely removed from the site. To prevent loss of the guidewire within the patient, the proximal portion the guide wire is typically specially constructed of a malleable substance with "memory," with suggested optional folding points within the proximal guidewire. These multiple folding points, once folded, will prevent loss of the guidewire through the puncture site and into the patient's body, where it would not be easily retrieved otherwise.

A sterile dressing may be placed over the external portion of the guide wire so as to maintain sterility. This guidewire placement serves several purposes. First, if one wants to reinsert a perfusion cannula, this guidewire could be used to do such. The folding points could be straightened and a catheter threaded back over the guide wire into position. Additionally puncture of the left ventricle may result in persistent bleeding at the puncture site. Percutaneous insertion of a puncture sealing device, such as used in noninvasive VSD closure, could be threaded down such a guidewire and could be used to close a leaking puncture site nonoperatively.

The drawing in FIG. 1A shows a completely closed system for left ventricular high pressure "jet" infusion of "cerebroplegic" solution, primarily targeting brain but beneficial too in preserving other organs in cardiac arrest primarily as a bridge to VA ECMO. The drawing shows the components of a fully embodied device. It is a closed system, since introduction of air at any time in the left ventricle can produce catastrophic results, resulting in air bubble embolization to critical organs, most specifically coronary arteries/heart and brain. The inventive device is also a closed system with high infusion pressure tolerance, to prevent disengagement during high-pressure infusion, with resulting leakage of infusion fluid and potential air entry into the left ventricle. The system is also closed to maintain sterility. The accompanying data (FIG. 2) shows that left ventricular pressure infusion through a 16-18 gauge catheter (used for testing) in an animal model causes good flow to the brain, making rapid cerebroplegia practical. With rapid cardio-cerebroplegia the brain is protected and also other organs, especially the heart, in that the heart would be rapidly cooled by the left ventricular infusion. As described above, too, the heart is also much more easily accessed than attempting to infuse through individual arteries supplying the brain. Also as described above, at risk individuals would likely have arteriosclerotic disease, and debris from plaques upon needle insertion would likely flow upstream into the brain and cause possibly irreparable damage. Four arteries supply the brain, the right carotid artery the left carotid artery the left vertebral artery and the right vertebral artery. With infusing in the left ventricle, all four arteries participate in perfusing the brain with the cerebroplegia solution. In addition, small diameter punctures of the left ventricle are known to be overwhelmingly self-sealing. By using a small-diameter puncture device, the chances of tissue damage upon imperfect insertion technique are minimized. Utilizing, high pressure infusion will entrain existing blood within the cardiovascular system to help perfuse vital organs. By using extremely cold infusion fluid, the resulting combined blood and infusion solution reach a therapeutic temperature cold temperature after mixing.

Referring again to FIG. 1, Module A is the infusion cannula; Module B is the trocar; Module C is the infusion reservoir and infusion pumping device; Module D is the infusion cannula position checking device; Module E is the wire insertion module; Module F is the sterile trocar retraction module; Module G is the trocar positioning verification module; and Module H provides for the optional guide wire hardware discussed above. As is clear from all of the above, the present cannula device would be inserted percutaneously through the left chest or upper abdomen into the left ventricle with the trocar fully extended inside the infusion cannula. By aspirating on the syringe pictured in module G, since the trocar is a hollow trocar with bird size at the tip once the tip is within a vascular structure one, would obtain a blood return through the bird's eye when the trocar is in correct position.

The following capsule summary reviews all of the above. The syringe will be partially filled with either a commonly used intravenous solution such as normal saline, or a cardioplegia solution (such as is known in the art for open heart surgery). In the context of the present invention, "cerebrocardioplegia solution" is any solution, including but not limited to prior art cardioplegia solution, that is able to be chilled and is compatible for introducing into the circulatory system of an animal or patient in need of the present hyperthermia treatment. Ultrasound using a Doppler mode could then be used to verify good position within the left ventricle by detecting flow generated by injecting into the hollow trocar with flow exiting into the left ventricle through the bird's eyes. The tips of the infusion cannula and trocar may be also composed of special echogenic materials which could be used additionally or alternatively to verify position of the infusion cannula and trocar within the left ventricle. The serial trocar retraction module is composed of clear plastic to visualize the process but also the specified length which upon full retraction does not enable the tip of the trocar to exit the system causing potential puncture issues but remain within the unused portion of the infusion cannula system. It also is a safety feature for the provider. By maintaining sterility the trocar could be reinserted into the infusion cannula if needed so that the cannula could be repositioned. Both the trocar and the infusion cannula would be rigid solid metal construction. This will better tolerate high-pressure infusion including reduction of catheter whip. A plastic catheter would not safely permit reintroduction of the trocar in that such devices are known to cause the catheter to be sheared. The tip of the trocar is not hollow so that a tissue core would not be created within the trocar and inadvertently embolized during any infusion procedure. Once the catheter position has been verified within the left ventricle and the trocar retracted infusion under high pressure may begin. Various solutions may then be infused with current data and practice, suggesting any such fluid should also be cooled. Module C is the infusion reservoir and infusion device. Various means of having the solution cooled could be employed and cold maintained with appropriate insulation. A motorized infusion pump could be used or a pneumatic pressure device such in high pressure intravenous infusions be used or even a mechanical piston device may be incorporated. If one would wish to further verify infusion cannula position after trocar retraction one could use module D to either aspirate blood or inject solution to verify cannula position by Doppler. Module G is a wire guide which can be inserted down the cannula and into the left ventricle to maintain the insertion tract should one wish to withdraw all the infusion cannula. The wire has a flexible removable flange enabling advancement through the infusion cannula. Upon exiting the tip of the infusion cannula the plan would unfurl preventing the wire from being lost within the patient. This option would enable upon removal of the flange Seldinger technique re-insertion of a another catheter or cannula or facilitate introduction of a left ventricular wall closure device upon restraightening of the "accordioned" external portion of the wire.

Figure 1B:
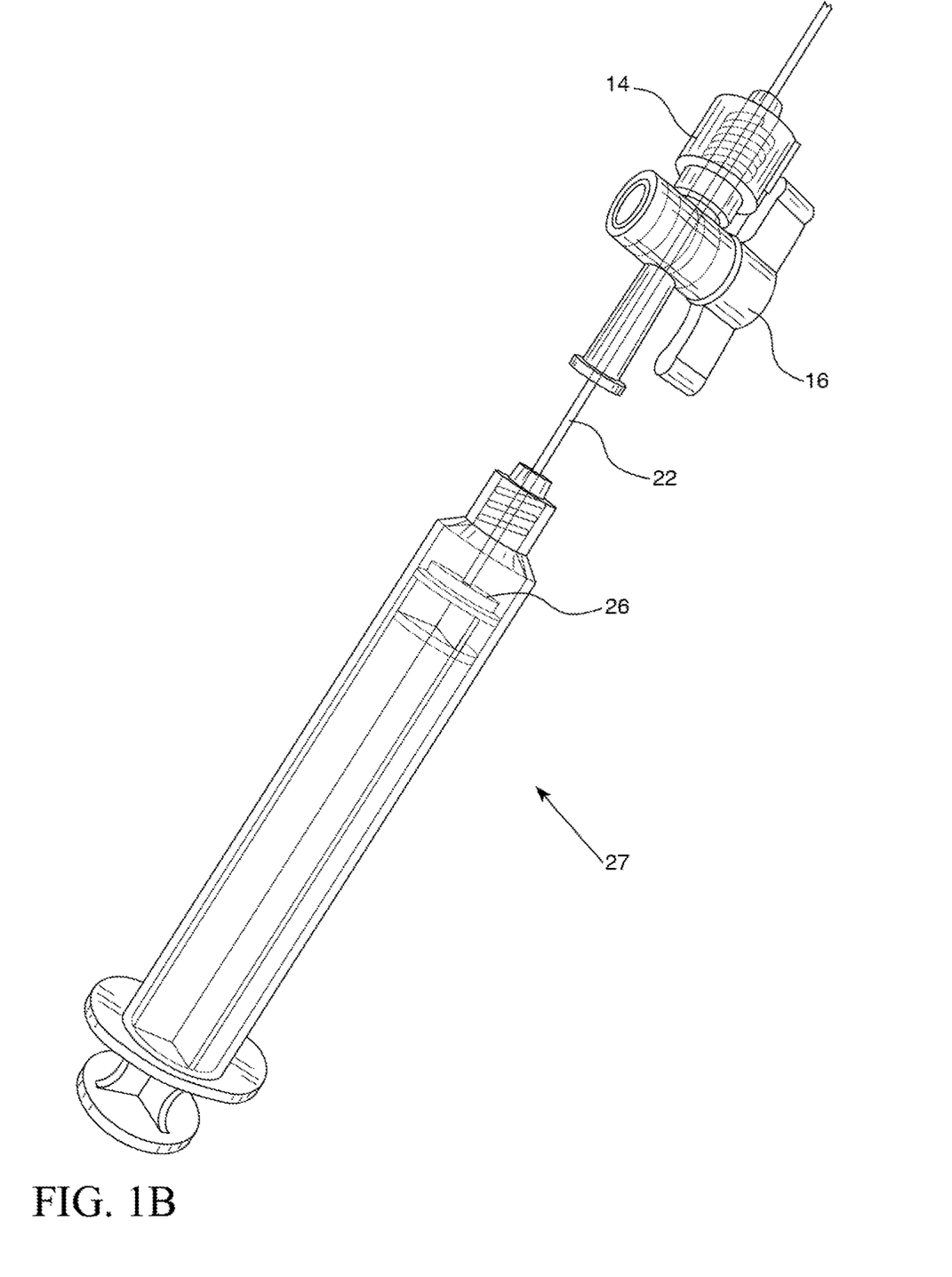
FIG. 1B is a perspective view of a trocar of the present invention, in position through a cooperating stopcock.

Referring now to FIG. 1B, an alternate embodiment of a trocar 22 has a trocar base 26 which is affixed to the interior plunger portion of a trocar syringe 27, so that the trocar may be extended and retracted via trocar syringe 27 instead of necessarily relying on the adaptability of flexible sheath 29. The trocar 22 extends, similarly as is shown in FIG. 1A, through the distal stopcock 16 (in open position) and likewise through the hollow center of the cannula fitting connector 14, and from thence through and to the cannula distal tip (not shown).

Figure 3A:
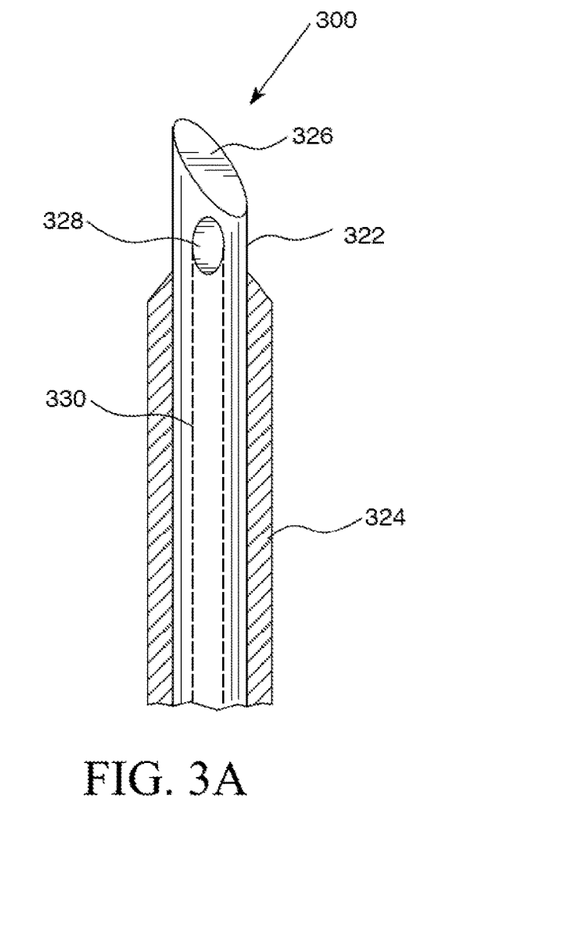
FIG. 3A is a perspective view of an embodiment of the present trocar, in which the cutting tip is solid and a partial hollow center ends in a "bird's eye" aperture near the cutting tip, with the trocar's being snugly fit within a surrounding cannula through which the trocar can shift and pass freely back and forth.
Figure 3B:
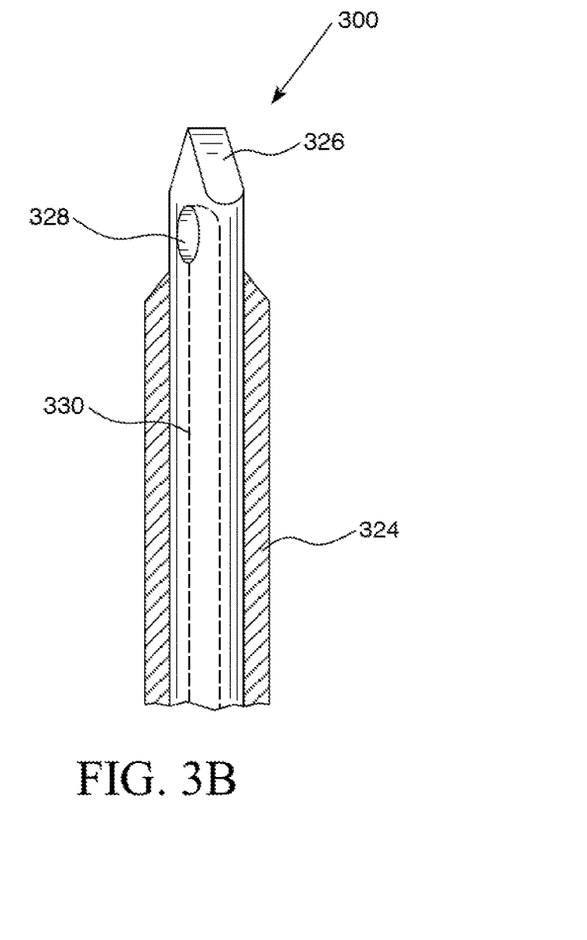
FIG. 3B is a perspective view of another geometric configuration of a cutting tip of a trocar, in which the cutting tip is roof-shaped and solid and a partial hollow center ends in a bird's eye aperture near the cutting tip, with the trocar's being snugly fit within a surrounding cannula through which the trocar can shift and pass freely back and forth.
Figure 3C:
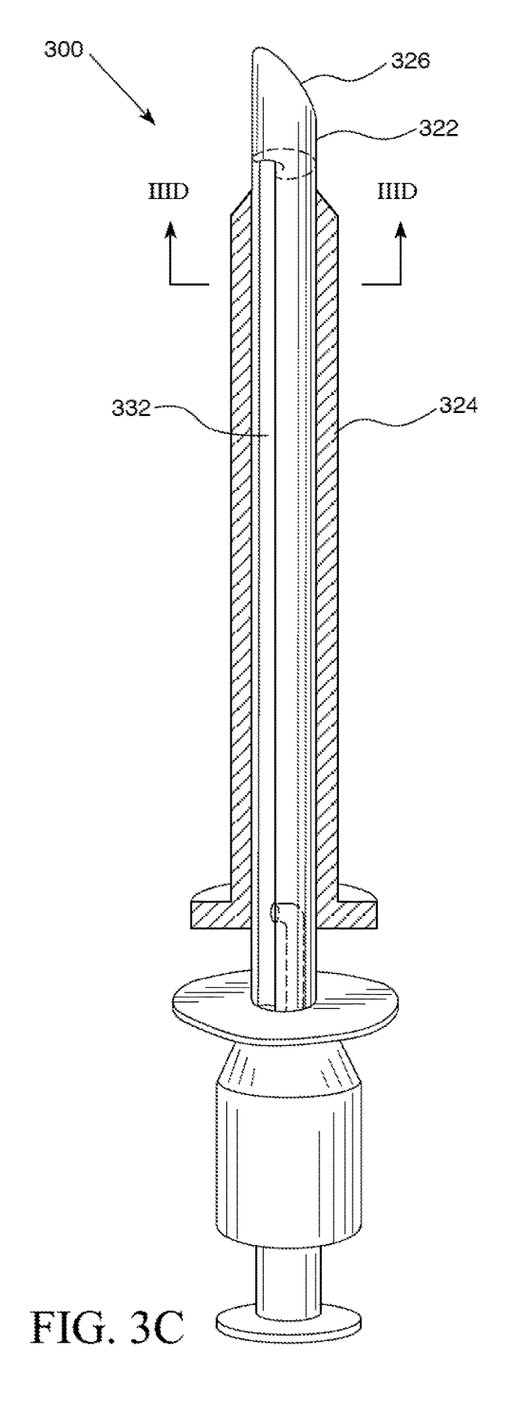
FIG. 3C is a perspective view of a trocar fitted with an exterior groove rather than an interior hollow center, snugly fit within a surrounding cannula.
Figure 3D:
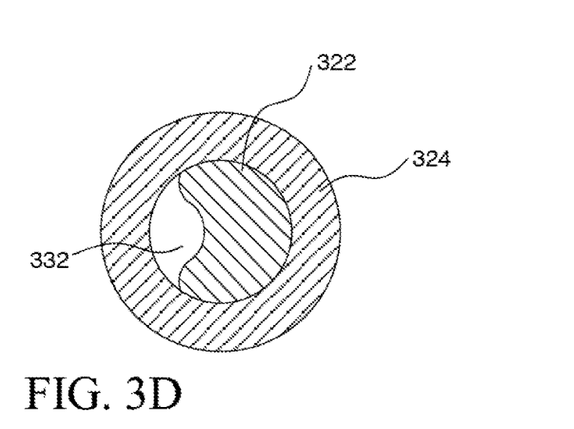
FIG. 3D is a sectional view along lines IIID-IIID of FIG. 3C.
Figure 3E:
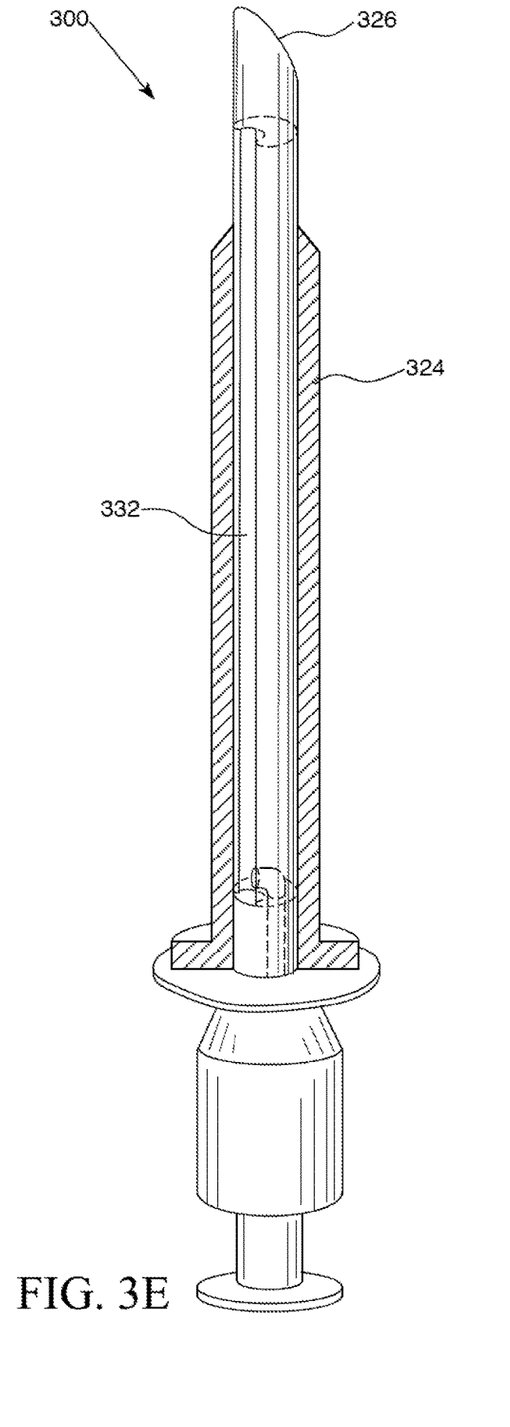
FIG. 3E is a perspective view of an alternative configuration of a trocar fitted with an external groove disposed within a surrounding cannula.
Figure 3F:
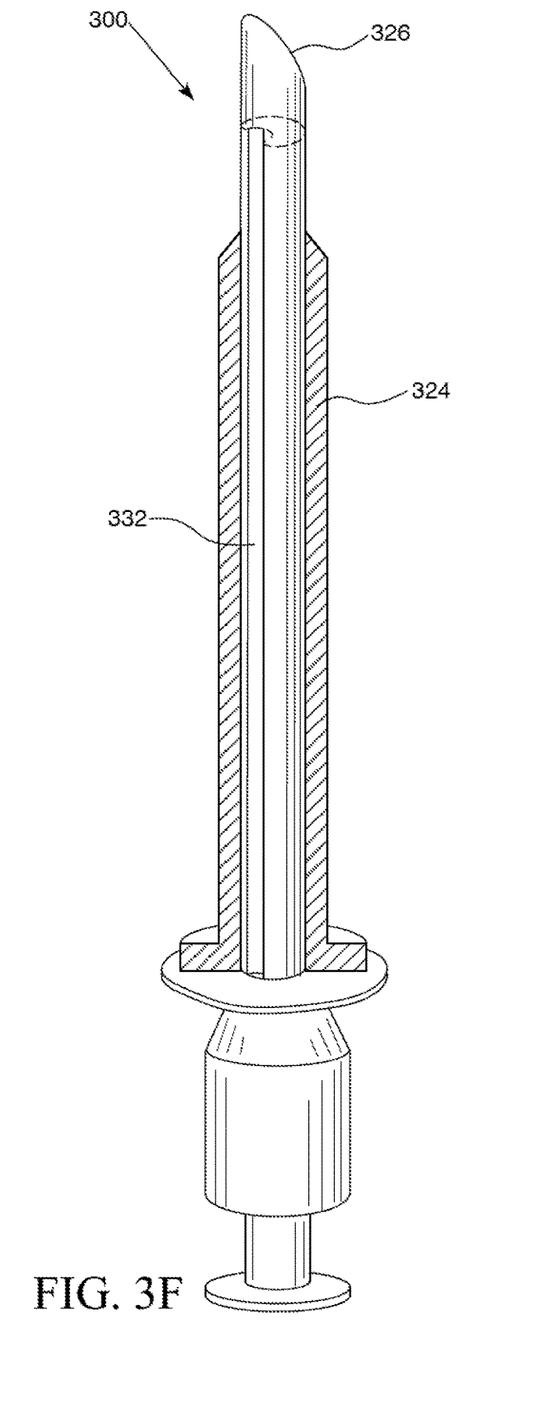
FIG. 3F is a perspective view of a further configuration of a trocar fitted with an external groove situated within a surrounding cannula.

FIGS. 3A-F show various embodiments of trocars in combination with their adjacent cannulas, both as to cutting tip shape as well as whether the channel leading to near the trocar tip is a hollow interior tube within the trocar, or a groove in the trocar that creates a hollow fluid tube within the cooperating cannula. In all of these figures, the trocar/cannula combination 300 has a trocar 322, an associated cannula 324 within which the trocar 322 can traverse in either direction, a trocar cutting tip 326, and either a trocar hollow center 330 or a trocar groove 332. FIGS. 3A and 3B contain bird's eye apertures 328. All of these structures and their functions have been discussed, above.

While it is possible to inject fluid with constant flow into the system, a preferred injection of cold fluid would be a pulsatile injection, such as from 60 to 100 pulses per minute. This pulsatile injection can be done manually or with a manually or computer controlled electric or other pump (see Module C of FIG. 1A). When pulsatile flow is introduced, about 30-50% of the pulse time would be actual fluid injection, balance "recovery." So, for pulsatile flow injection of 60 pulses per minute, approximately 0.3-0.5 seconds would be fluid injection and the rest would be a recovery period during which the left ventricle could retract and refill or otherwise equilibrate. Pulsatile flow enhances cooling by facilitating mixing of the cold fluid faster into the fluid flows within the patient, whereas direct uninterrupted flow does is believed not to facilitate mixing as well.

Although the invention has been described with particularity above, it is only to be limited insofar as is set forth in the accompanying claims.

I claim:

1. A percutaneous transmyocardial jet perfusion device, comprising: a cooperating trocar and a cannula device for the perforation and cannulation of the left ventricle of the heart of a patient or animal in need of such treatment, wherein said cooperating trocar is initially secured within a stopcock; a fluid reservoir charged with a quantity of fluid, wherein said quantity of fluid is maintained in a chilled state; a portable pump; and a testing syringe, wherein all cooperating elements portions of the cooperating trocar and cannula device are housed within a sterile closed system incorporating a flexible sheath in which said cooperating trocar can advance and retract.

2. The device according to claim 1, wherein said cooperating trocar has a solid cutting tip.

3. The device according to claim 2, wherein said cooperating trocar has a bird's eye aperture adjacent the solid cutting tip.

4. The device according to claim 3, wherein said bird's eye aperture connects to a hollow tube within said cooperating trocar.

5. The device according to claim 3, wherein said bird's eye aperture connects to a groove in said cooperating trocar, and said groove forms a fluid channel in association with said cannula device.

6. The device according to claim 3, wherein said cooperating trocar is retractable through said cannula device.

7. The device according to claim 3, wherein said cannula device contains an associated guide wire.

8. The device according to claim 3, wherein said testing syringe is an aspiration syringe.

9. The device according to claim 3, wherein said portable pump is a manual pump.

10. The device according to claim 3, wherein said portable pump is a powered pump.

11. The device according to claim 3, wherein said portable pump is configured to provide pulsatile fluid flow.

12. The device according to claim 3, wherein said portable pump is configured to provide pulsatile fluid flow of between 60 to 100 pulses per minute.

13. The device according to claim 3, wherein said portable pump is configured to provide pulsatile fluid flow wherein a pulse created by said portable pump has a duticycle wherein 30-50% of the periodicity of the pulsatile flow represents active pumping.

* * * * *